US00PP26830P3

(12) United States Plant Patent
Van Swieten

(10) Patent No.: US PP26,830 P3
(45) Date of Patent: Jun. 14, 2016

(54) ***PHALAENOPSIS* ORCHID PLANT NAMED 'PHALDUZAH'**

(50) Latin Name: *Phalaenopsis Blume*
Varietal Denomination: PHALDUZAH

(71) Applicant: ANTHURA B.V., Bleiswijk (NL)

(72) Inventor: Martinus Nicolaas Gerardus Van Swieten, Den Haag (NL)

(73) Assignee: ANTHURA B.V., Bleiswijk (NL)

( * ) Notice: Subject to any disclaimer, the term of this patent is extended or adjusted under 35 U.S.C. 154(b) by 70 days.

(21) Appl. No.: 14/544,039

(22) Filed: Nov. 18, 2014

(65) Prior Publication Data

US 2016/0143200 P1 May 19, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Mar. 17, 2016. p. 1.*

* cited by examiner

*Primary Examiner* — Annette Para
(74) *Attorney, Agent, or Firm* — Jondle & Associates, P.C.

(57) ABSTRACT

A new and distinct variety of *Phalaenopsis* plant named 'PHALDUZAH', particularly characterized by having white flowers with purple flecks, typically 2 peduncles, an inflorescence that is long and sturdy, leaves that are oblong shape, and is propagated by tissue culture is disclosed.

3 Drawing Sheets

Genus and species: *Phalaenopsis* Blume.
Variety denomination: 'PHALDUZAH'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDUZAH'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicle, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDUZAH' is particularly characterized by its attractive and unique white flowers with purple flecks, economical propagation by tissue culture, rapid growth, and a plant dimension suitable for packaging and shipping to the market.

'PHALDUZAH' is a product of a planned breeding program conducted in Bleiswijk, The Netherlands.

The new *Phalaenopsis* 'PHALDUZAH' originated from a cross made in August 2005 in Bleiswijk, The Netherlands. The female parent is a white flecked *Phalaenopsis* pot plant named '00001-1758' (unpatented), while the male parent is a white *Phalaenopsis* pot plant named '06541-0001' (unpatented). A single plant was selected in January 2009 and has been asexually reproduced repeatedly by tissue culture in Bleiswijk, The Netherlands over a 2.5-year period. The new variety has been found to retain its distinctive characteristics through successive asexual propagations.

Asexual reproduction of 'PHALDUZAH' by tissue culture was first performed in January 2012 in Bleiswijk, The Netherlands and has demonstrated that the new cultivar is firmly fixed and retained through successive generations of asexual reproduction.

Plant Breeder's Rights for this variety have been applied for in Europe on Apr. 25, 2014. 'PHALDUZAH' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) White flowers with purple flecks;
2) Typically 2 peduncles;
3) Inflorescence is long and sturdy;
4) The shape of the leaves is oblong; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in August 2014.

DESCRIPTION OF THE NEW VARIETY

Figure 1:
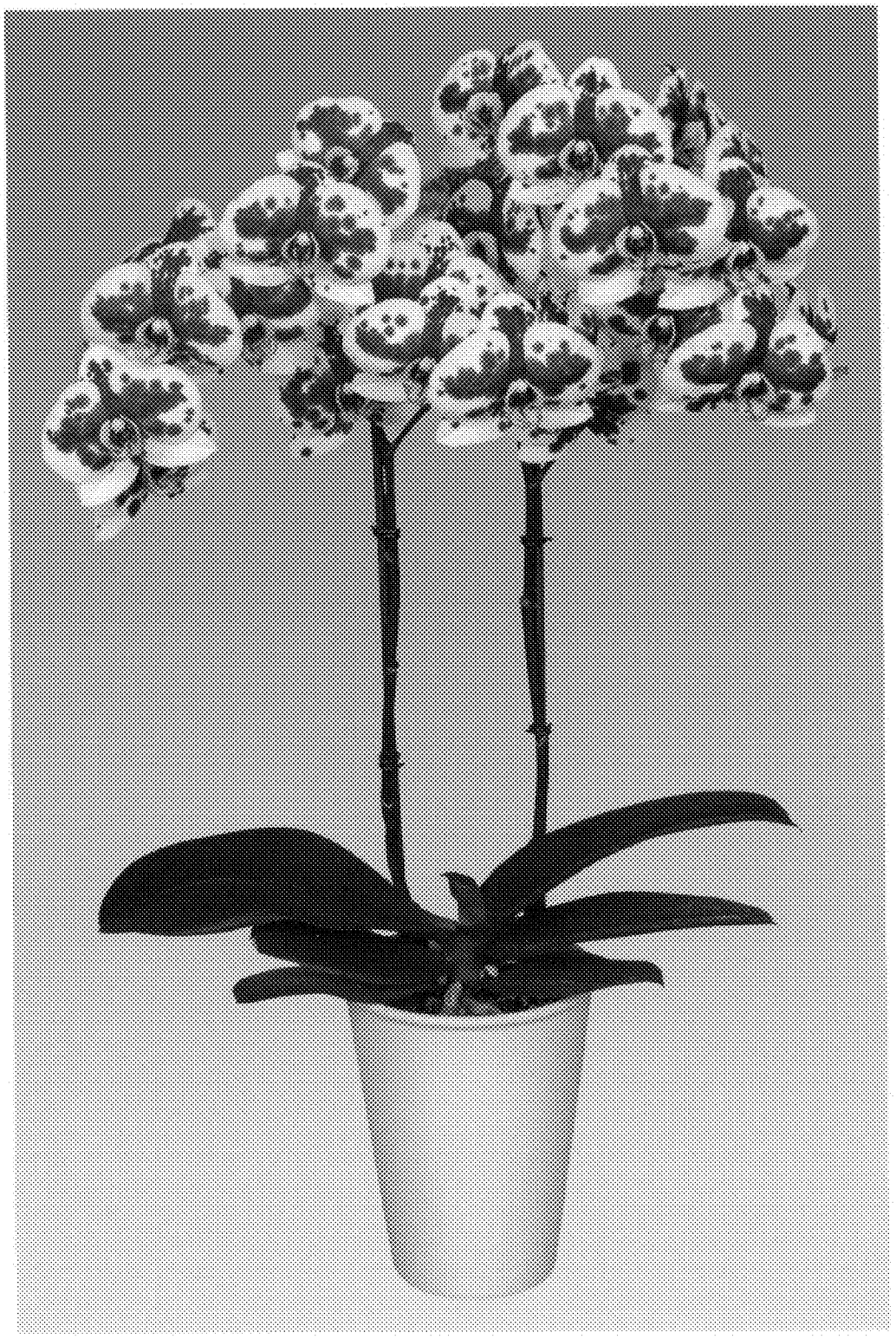
FIG. 1 shows the overall plant habit, including blooms, buds and foliage of 'PHALDUZAH'.
Figure 2:
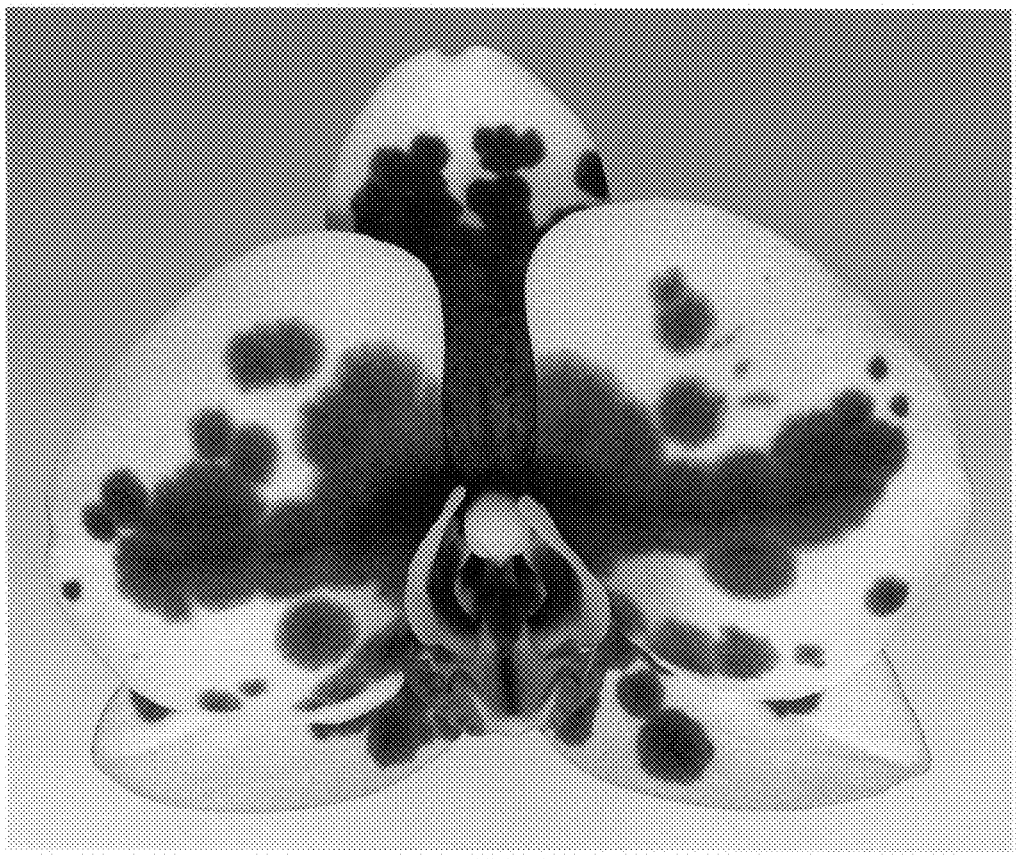
FIG. 2 shows a close-up of a flower of 'PHALDUZAH'.
Figure 3:
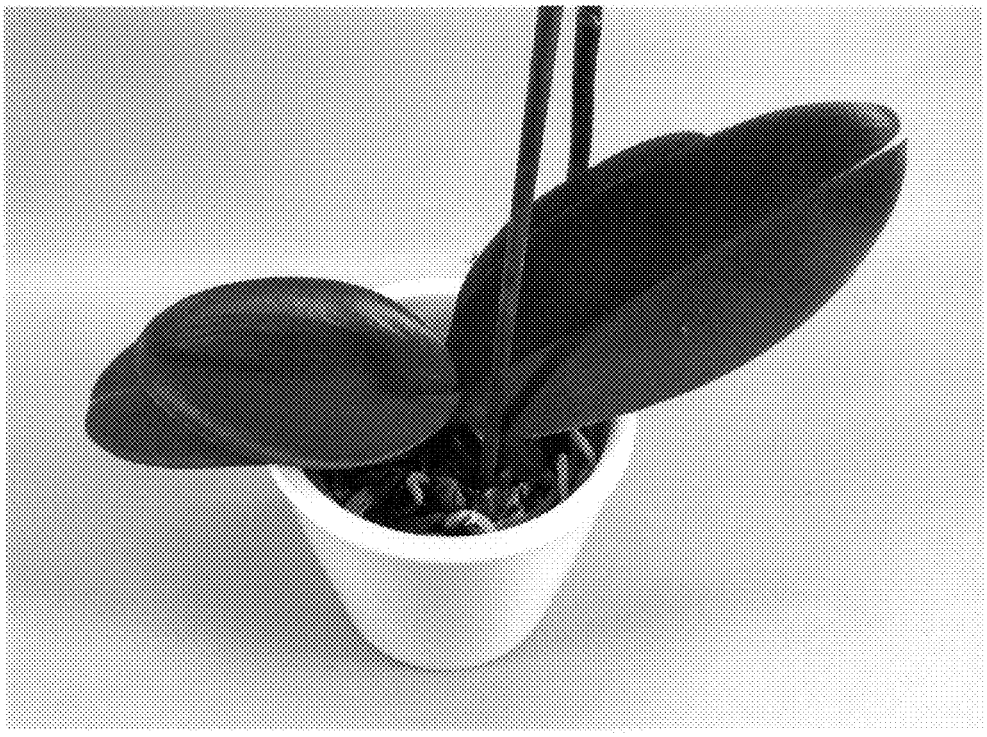
FIG. 3 shows a close-up of the leaves of 'PHALDUZAH'.

The following detailed description sets forth the distinctive characteristics of 'PHALDUZAH'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in August 2014. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Orchidaceae.
- *Botanical*.—*Phalaenopsis* Blume.
- *Common name*.—*Phalaenopsis*.
- *Variety name*.—'PHALDUZAH'.

Parentage:
- *Female parent*.—*Phalaenopsis* cultivar '00001-1758' (unpatented).
- *Male parent*.—*Phalaenopsis* cultivar '06541-0001' (unpatented).

Propagation:
- *Type*.—Tissue culture.

Plant:
- *Crop time* (*time to produce a finished flowering plant*).—48 to 50 weeks for a 12 cm pot.
- *Growth habit of inflorescence*.—Standard, green leaves and raceme to panicle.
- *Height* (*including pot, including inflorescence*).—55.0 cm to 65.0 cm.
- *Width* (*measured from leaf tips*).—32.0 cm to 36.0 cm.
- *Vigor*.—Strong.

Roots:
- *Root description*.—Grey-green-colored roots with light branching lateral roots having grey-green-colored root tips.

Leaves:
- *Mature leaves*.—Quantity per plant: 7 to 8 leaves are produced before flowering. Length (fully expanded): 14.0 cm to 19.0 cm. Width: 7.5 cm to 8.5 cm. Shape: Oblong. Apex: Unequal mucronate. Leaf blade angle with the petiole: Between 5 degrees and 20 degrees. Leaf margin: Entire. Color: Upper surface: RHS 147A. Lower surface: RHS 146A. Texture: Slightly rough. Thickness: 2.8 mm to 3.1 mm. Venation: Pattern: Parallel. Color of the midvein: Upper surface: RHS 147A. Lower surface: RHS 146A.

Peduncle:
- *Quantity per plant*.—Typically 2.
- *Number of flowers per peduncle*.—9 to 14.
- *Length*.—56.0 cm to 66.0 cm.
- *Diameter*.—5.9 mm.
- *Strength*.—Strong.
- *Aspect*.—Upright to pendent.
- *Texture*.—Slightly rough.
- *Color*.—Green/grey-brown (RHS 191A and 200A).
- *Internode length*.—50.0 mm to 60.0 mm.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 230.0 mm to 280.0 mm. Diameter: 3.7 mm to 4.0 mm.
- *Flowering time*.—First flowers can be expected 10 to 11 months after planting in a 12 cm pot.
- *Flower*.—Note: The number and intensity of flecks/spots on the flower may vary depending on the temperature. Height: 80.0 mm to 85.0 mm. Diameter: 85.0 mm to 90.0 mm. Depth of lip: 20.0 mm to 22.0 mm.
- *Flower longevity*.—On the plant: 12 to 16 weeks.
- *Fragrance*.—Absent.
- *Petals*.—Arrangement: Open. Shape: Semi-circular. Apex: Emarginate and slightly asymmetric. Margin: Entire. Length (from base to tip): 39.0 mm to 41.0 mm. Width: 57.0 mm to 59.0 mm. Color (when fully opened): Main color: White (RHS 155C) with flecks of purple (RHS between 78A and 79A). At the base: White (RHS 155C) with flecks of purple (RHS between 78A and 79A).
- *Dorsal sepal*.—Shape: Broad elliptic. Margin: Entire. Length (from base to tip): 42.0 mm to 44.0 mm. Width: 30.0 mm to 32.0 mm. Color (when fully opened): Main color: White (RHS 155C) with flecks of purple (RHS between 78A and 79A). At the base: White (RHS 155C) with flecks of purple (RHS between 78A and 79A).
- *Lateral sepals*.—Shape: Ovate. Margin: Entire. Length (from base to tip): 46.0 mm to 48.0 mm. Width: 30.0 mm to 32.0 mm. Color (when fully opened): Main color: White (RHS 155C) with flecks of purple (RHS between 78A and 79A). At the base: White (RHS 155C) with flecks of purple (RHS. between 78A and 79A).
- *Labellum* (*lip*).—Margin: Entire. Length: 20.0 mm to 22.0 mm. Width: 19.0 mm to 21.0 mm.
- *Lateral lobe*.—Shape: Type V (as described in the International Union for the Protection of New Varieties of Plants (UPOV) Test Guidelines for *Phalaenopsis*). Color: Central lobe dark purple (RHS 187A) and lighter colors towards the tip of yellow (RHS 12C) and white (RHS 155C).

*Apical lobe*.—Shape: Obdeltoid. Color: Base is yellow (RHS 4A) with stripe in the middle (RHS 71A), both sides are light purple (RHS 78D) toward the tip, with purple whiskers (RHS 71A) having yellow tips (RHS 9A).

*Callus*.—Color: Dark purple (RHS 187A).

*Pedicel*.—Length: 35.0 mm to 37.0 mm. Diameter: 2.7 mm to 3.7 mm.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 9.0 mm to 11.0 mm. Diameter: 5.4 mm to 5.9 mm. Color: Purple (RHS 78A).

*Pollinia*.—Quantity: 2. Size: 0.9 mm to 1.1 mm. Color: Orange (RHS 26A).

*Ovary*.—Length: 15.0 mm to 17.0 mm. Diameter: 2.4 mm to 2.6 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDUZAH' differs from male parent '06541-0001' (unpatented) in that 'PHALDUZAH' has a flower that is smaller and flecked with color, whereas '06541-0001' has a flower that is bigger and evenly colored. Additionally, 'PHALDUZAH' has a dark purple callus and a green/grey-brown peduncle, whereas '06541-0001' has a yellow, spotted callus and a green peduncle.

'PHALDUZAH' differs from commercial variety 'PHALMOQXIM' (unpatented) in that 'PHALDUZAH' has a bigger flower and purple whiskers of the apical lobe, whereas 'PHALMOQXIM' has a smaller flower and white whiskers of the apical lobe. Additionally, 'PHALDUZAH' has a yellow base of the apical lobe that is purple towards the tip, whereas 'PHALMOQXIM' has a yellow base of the apical lobe that is white towards the tip.

I claim:

1. A new and distinct variety of *Phalaenopsis* plant named 'PHALDUZAH', substantially as described and illustrated herein.

* * * * *